United States Patent [19]

Tadano et al.

[11] Patent Number: 5,700,652
[45] Date of Patent: Dec. 23, 1997

[54] QUANTITATIVE DETERMINATION METHOD FOR SODIUM IONS

[75] Inventors: Toshio Tadano, Numazu; Akira Miike, Shizuoka; Jun Umemoto, Miki, all of Japan

[73] Assignee: Kyowa Medex Co., Ltd., Tokyo, Japan

[21] Appl. No.: 530,336

[22] PCT Filed: Apr. 6, 1994

[86] PCT No.: PCT/JP94/00572

§ 371 Date: Nov. 29, 1995

§ 102(e) Date: Nov. 29, 1995

[87] PCT Pub. No.: WO94/23061

PCT Pub. Date: Oct. 13, 1994

[30] Foreign Application Priority Data

Apr. 7, 1993 [JP] Japan ................... 5-080817

[51] Int. Cl.[6] .................. C12Q 1/54; C12Q 1/00; C12Q 1/34; C12Q 1/48
[52] U.S. Cl. ................. 435/14; 435/4; 435/18; 435/15; 436/63; 436/74; 436/79
[58] Field of Search ................... 435/14, 4, 18, 435/15; 436/63, 74, 79

[56] References Cited

U.S. PATENT DOCUMENTS

| | | | |
|---|---|---|---|
| 5,196,306 | 3/1993 | Bobrow et al. | 435/7.9 |
| 5,380,649 | 1/1995 | Berry et al. | 435/14 |
| 5,384,246 | 1/1995 | Berry et al. | 435/18 |
| 5,384,247 | 1/1995 | Berry et al. | 435/14 |
| 5,409,814 | 4/1995 | Berry et al. | 435/18 |
| 5,501,958 | 3/1996 | Berry et al. | 435/18 |

*Primary Examiner*—Louise Leary
*Attorney, Agent, or Firm*—Fitzpatrick, Cella, Harper & Scinto

[57] ABSTRACT

The present invention relates to a method for quantitatively determining sodium ions in a sample using β-galactosidase in an aqueous medium, wherein a β-galactosidase reaction is carried out in the presence of a cation which competes with the sodium ion.

The method of the present invention is good in accurate determination and reproducibility and enables the simple and quick quantitative determination of sodium ions.

4 Claims, 5 Drawing Sheets

QUANTITATIVE DETERMINATION METHOD FOR SODIUM IONS

TECHNICAL FIELD

This invention relates to a method for quantitatively determining sodium ions using β-galactosidase in the presence of a cation which competes with the sodium ion.

BACKGROUND ART

As a method for chemically determining the amount of sodium ions in a biosample, there is known a method utilizing a β-galactosidase reaction which increases enzyme activity in proportion to the amount of sodium ions. In this method, Cryptfix™ 221 is used to prevent the enzyme reaction from being saturated with excessive sodium ions [Clinical Chemistry, 34:2295 (1988)]. There is also disclosed a method wherein lithium ion is used instead of Cryptfix™ 221 in the above-mentioned determination method, but no concrete example is disclosed which uses lithium ion alone (Japanese Unexamined Patent Publication/PCT No. 1-503596) (Dec. 7, 1989).

A method using a bicyclic crown ether such as Cryptfix™ 221 has the following character. Since the dissociation rate of the cryptate is small, a long time is needed for the prereaction before the start of measurement. Therefore, the operation of the method is not simple. In addition, since Cryptfix™ 221 is preincubated with β-galactosidase because of the above-mentioned reasons, the stability of β-galactosidase is damaged by Cryptfix™ 221 and it becomes impossible to quantitatively determine sodium ions at a low concentration. Furthermore, the pH of the reaction solution is restricted to the alkaline area. In view of these problems, the development of a better method for quantitative determination of sodium ions is desired.

DISCLOSURE OF THE INVENTION

The present invention relates to a method for quantitatively determining sodium ions in a sample using β-galactosidase in an aqueous medium, which method is characterized in that a β-galactosidase reaction is carried out in the presence of a cation which competes with the sodium ion.

In the present invention, "an aqueous medium" means a liquid containing water, such as a buffer and physiological saline. As examples of the buffer, tris(hydroxymethyl) aminomethane-HCl buffer (hereinafter referred to as "Tris-HCl buffer"), phosphate buffer, acetate buffer, succinate buffer, oxalate buffer, phthalate buffer, borate buffer, glycine buffer, barbital buffer, Good's buffer and the like may be enumerated.

As the sample containing sodium ions, any sample may be used as long as it is miscible with an aqueous medium. Biosamples such as whole blood and cells that are difficult to measure by the atomic absorption spectrometry, the flame photometry or the like can be measured by the present invention.

As the cation which competes with the sodium ion, an alkali metal ion, such as lithium, potassium, rubidium or cesium ion, or ammonium ion may be enumerated. These ions may be used independently or in combination. The suitable concentration of the cation which competes with the sodium ion is 130 mM - 0.5M for lithium ion, 20 mM–200 mM for potassium ion, 120 mM–500 mM for cesium ion, 20 mM–500 mM for rubidium ion and 50 mM–500 mM for ammonium ion.

As a source for lithium or potassium ions, chlorides, nitrates, sulfates, borohydride of these ions and the like may be enumerated. As a source for rubidium or cesium ions, chlorides of these ions and the like may be enumerated. As a source for ammonium ions, ammonium sulfate, ammonium chloride and the like may be enumerated.

The β-galactosidase in the present invention may be any enzyme as long as it belongs to the enzyme number EC. 3.2.1.23. A β-galactosidase derived from an animal, microorganism or plant, as well as an enzyme which is obtained by modifying such a β-galactosidase with genetic engineering techniques are included.

As a substrate for β-galactosidase, either synthetic or natural substrates may be used. For example, β-D-galactoside, aryl β-D-galactoside, alkyl β-D-galactoside, 3,6-dihydroxyfluoran β-D-galactoside, nitrophenyl β-D-pyranoglycoside, nitrophenyl β-D-galactoside, lactinol, lactose, 4-methylumbelliferyl β-D-galactoside and the like may be enumerated. As an activator for β-galactosidase, magnesium sulfate, magnesium chloride, magnesium nitrate or the like is used.

The amount of a substrate for β-galactosidase decreases in the reaction solution. Changes of the amount of a substrate for β-galactosidase, can be determined by measuring the decrease of the substrate, such as nitrophenyl β-D-galactoside mentioned above, by the absorptiometry or the like.

The amount of reaction products can be determined by measuring galactose, aglycone, 3,6-dihydroxyfluoran, nitrophenol, etc. which generated from the substrate, by the colorimetry absorptiometry, fluorophotometry, oxidation-reduction measuring method, high performance liquid chromatography or the like. Alternatively, β-galactosidase reaction may be coupled with galactose dehydrogenase or the like and the reduction type coenzyme produced may be quantitatively determined.

Now, preferable embodiments of the method of the present invention for quantitatively determining sodium ions will be described below.

To the above-mentioned buffer solution (50–1000 mM/l solution: pH 5.0–9.5), a cation which competes with sodium ion, magnesium ion (1–20 mM) and a sample are added. To the resultant solution, 1–12 mM of a substrate for β-galactosidase or 200–7500 unit/l of β-galactosidase is added and prereacted at 8°–50° C. for 1 second or more. Next, in the case where β-galactosidase has been added, 1–12 mM of a substrate for β-galactosidase is added thereto, and in the case where a substrate for β-galactosidase has been added, 200–7500 unit/l of β-galactosidase is added thereto. Then, the resultant solution is reacted at 8°–50° C. for 1 second or more. The amount of the substrate for β-galactosidase which decreases in the reaction solution is determined as described above, or the amount of a β-galactosidase reaction product produced in the reaction solution is determined as described above to thereby determine the amount of the substrate which has been consumed in the β-galactosidase reaction. In this enzyme reaction, an amount of the substrate which is equivalent to the amount of sodium ions in the sample is consumed. Therefore, the amount of sodium ions can be determined according to the above-mentioned determination method.

In the practice of the method of the present invention, a surfactant such as Triton X-100 may be added, if necessary, to prevent the occurrence of turbidity in the reaction solution. In addition, if necessary, bovine serum albumin (BSA) or human serum albumin (HSA) may be added which reduces the influence of the albumin contained in the sample and also works as a solubilizing agent. Furthermore, proteins such as human immunoglobulin and ovalbumin, solubilizing agents such as dimethyl sulfoxide, and antioxidants such as dithiothreitol may be added, if necessary.

In order to eliminate the interference of di- or trivalent metals and to enhance the effect of the cation which competes with the sodium ion, a chelating agent such as ethylenebis(oxyethylenenitrilo)tetraacetic acid (EGTA) and ethylenediaminetetraacetic acid (EDTA) may be used in the method of the present invention. In addition, in order to improve the accuracy in the determination and to enhance the effect of the cation which competes with the sodium ion, a binder for sodium ions such as a monocyclic crown ether may also be added. As the monocyclic crown ether, 18-crown-6, N-[2-(methoxy)ethyl]monoaza-15-crown-5, N-[2-(2-methoxyethoxy)ethyl]monoaza-15-crown-5 are typically used. The concentration of the monocyclic crown ether is usually 5–100 mM, preferably 10–50 mM. By adding these chelating agent and binder, it is possible to lower the suitable concentration of the cation competitive with the sodium ion.

The cation which competes with the sodium ion used in the present invention reduces the activity of the sodium ions in the sample to such an extent that is necessary and sufficient. Therefore, a prereaction before the start of measurement does not require much time in the quantitative determination method of the present invention. In addition, it is not necessary to preincubate the cation with β-galactosidase. Accordingly, the stability of β-galactosidase is not damaged and the measurement can be performed with this enzyme being in a stable condition. In addition, the applicable pH range of they method of the present invention is broader compared to the reaction using Cryptfix™. Therefore, according to the present invention, there is provided a novel method for quantitatively determining sodium ions in a biosample which method is quick, simple and good in accurate determination.

BEST MODE FOR CARRYING OUT THE INVENTION

The present invention will be described in more detail below with reference to the following Examples, which should not be construed as limiting the scope of the present invention.

(EXAMPLE 1)

(1) Preparation of Standard Solutions for Determining Sodium Ion Calibration Curves Sodium chloride (Wako Pure Chemicals) was diluted with distilled water to prepare standard solutions for determining calibration curves for 100–180 mM sodium ions contained in reaction solutions.

Figure 1:
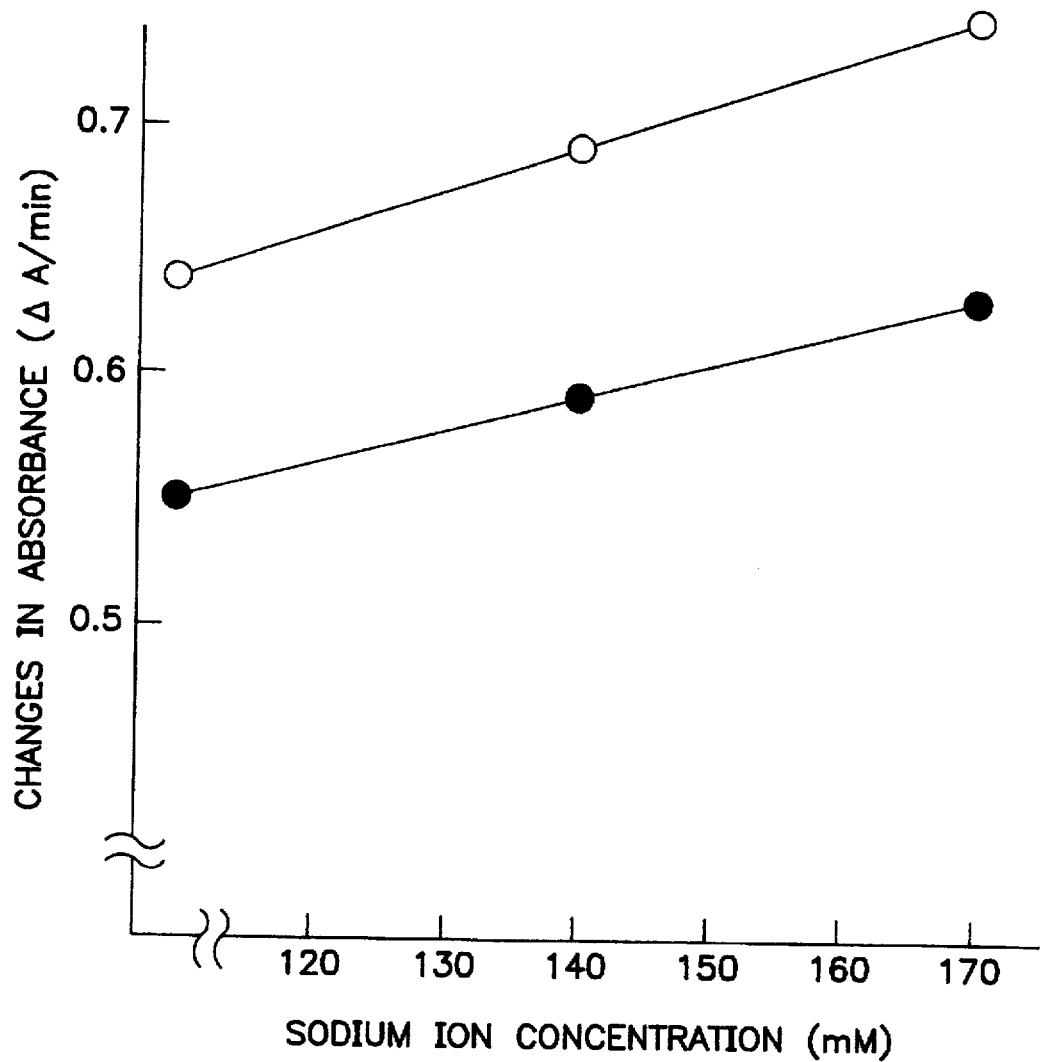
FIG. 1 shows calibration curves for sodium ions obtained by using 220 mM or more of lithium ions. In the FIG. 1, marks -○- and -●- represent the calibration curves for sodium ions when the lithium ion concentrations are 220 mM and 260 mM, respectively.

(2) Quantitative Determination of Sodium Ions 0.05 ml of the standard solution of sodium ion was placed in a test tube. Then, 2.0 ml of 300 mM Tris-HCl buffer (pH 7.4) preheated to 37° C. and containing 1100 unit/l β-galactosidase (Sigma), 3 mM DL-dithiothreitol (Sigma), 11.2 mM magnesium sulfate (Sigma) and 220 mM or 260 mM lithium chloride (Wako Pure Chemicals) was added to the test tube. Then, 1.0 ml of distilled water preheated to 37° C. and containing 1.5 mM o-nitrophenyl β-D-pyranoglycoside (Merck) was added thereto, mixed with agitation, and reacted at 37° C. The amount of o-nitrophenol produced for 1 minute was determined with a spectrophotometer (Hitachi; Model UV3400) based on the absorption intensity of the visible portion at 420 nm. The calibration curves obtained are shown in FIG. 1.

(EXAMPLE 2)

Figure 2:
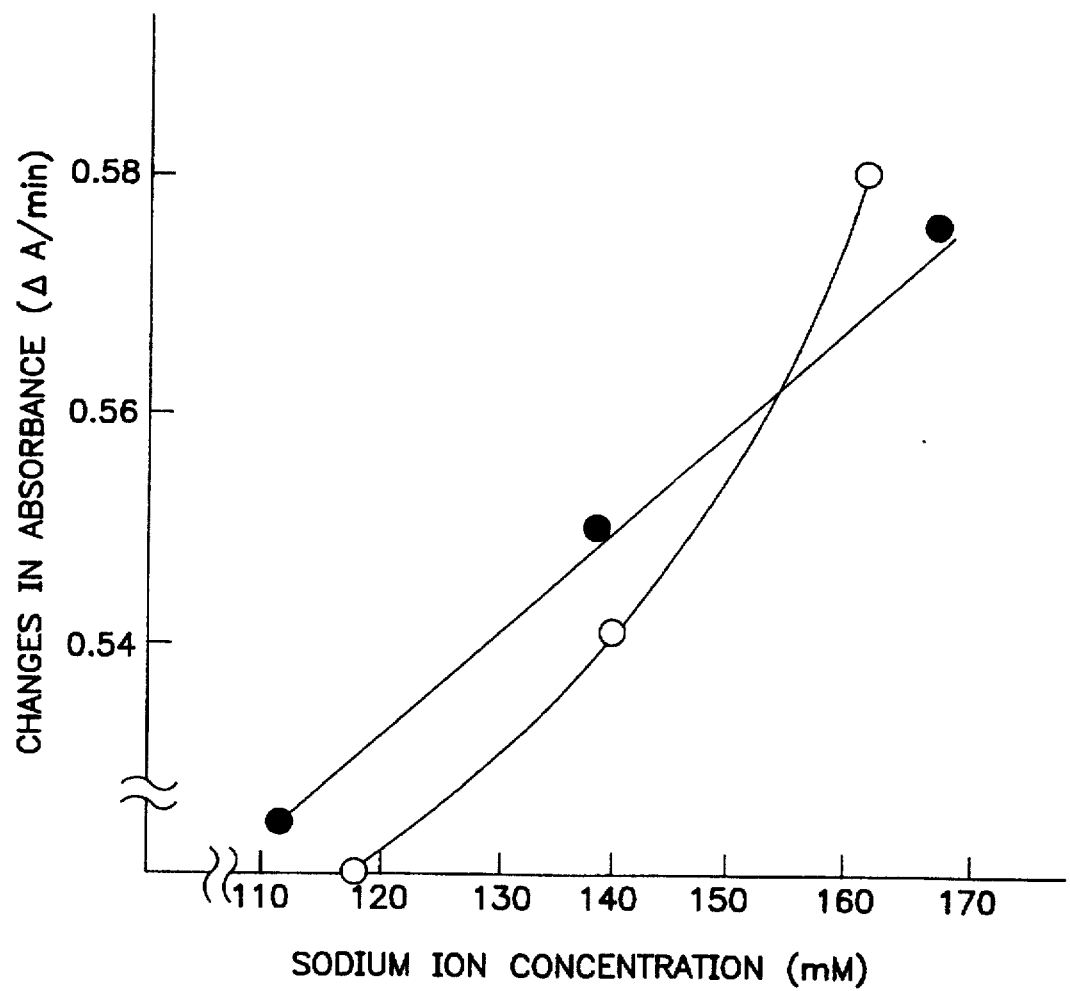
FIG. 2 shows calibration curves for sodium ions obtained by using 130 mM or less of lithium ions. In the FIG. 2, marks -○- and -●- represent the calibration curves for sodium ions when the lithium ion concentrations are 90 mM and 130 mM, respectively.

Sodium ions were quantitatively determined in the same manner as in Example 1 except that the lithium chloride concentration was changed to 90 mM or 130 mM. The calibration curves obtained are shown in FIG. 2.

Lithium chloride exhibited linearity at a concentration of 130 mM.

(EXAMPLE 3)

Figure 3:
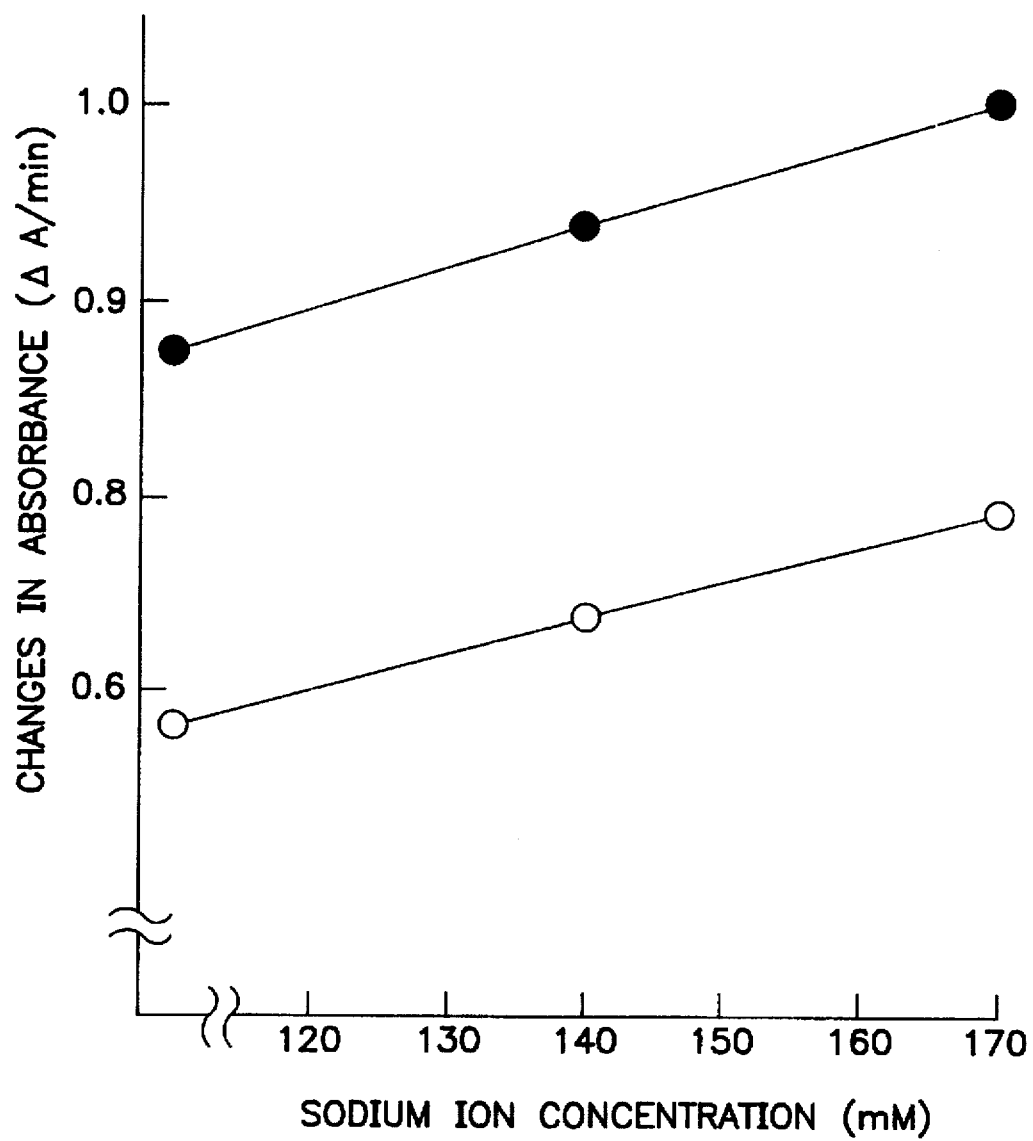
FIG. 3 shows calibration curves for sodium ions obtained by using potassium ions. In the FIG. 3, marks -○- and -●- represent the calibration curves for sodium ions when the concentrations of o-nitrophenyl β-D-pyranoglycoside are 1.5 mM and 3 mM, respectively.

Sodium ions were quantitatively determined in the same manner as in Example 1 except that 50 mM potassium chloride was used instead of lithium chloride and that the o-nitrophenyl β-D-pyranoglycoside concentration was 1.5 mM or 3 mM. The calibration curves obtained are shown in FIG. 3.

(EXAMPLE 4)

Figure 4:
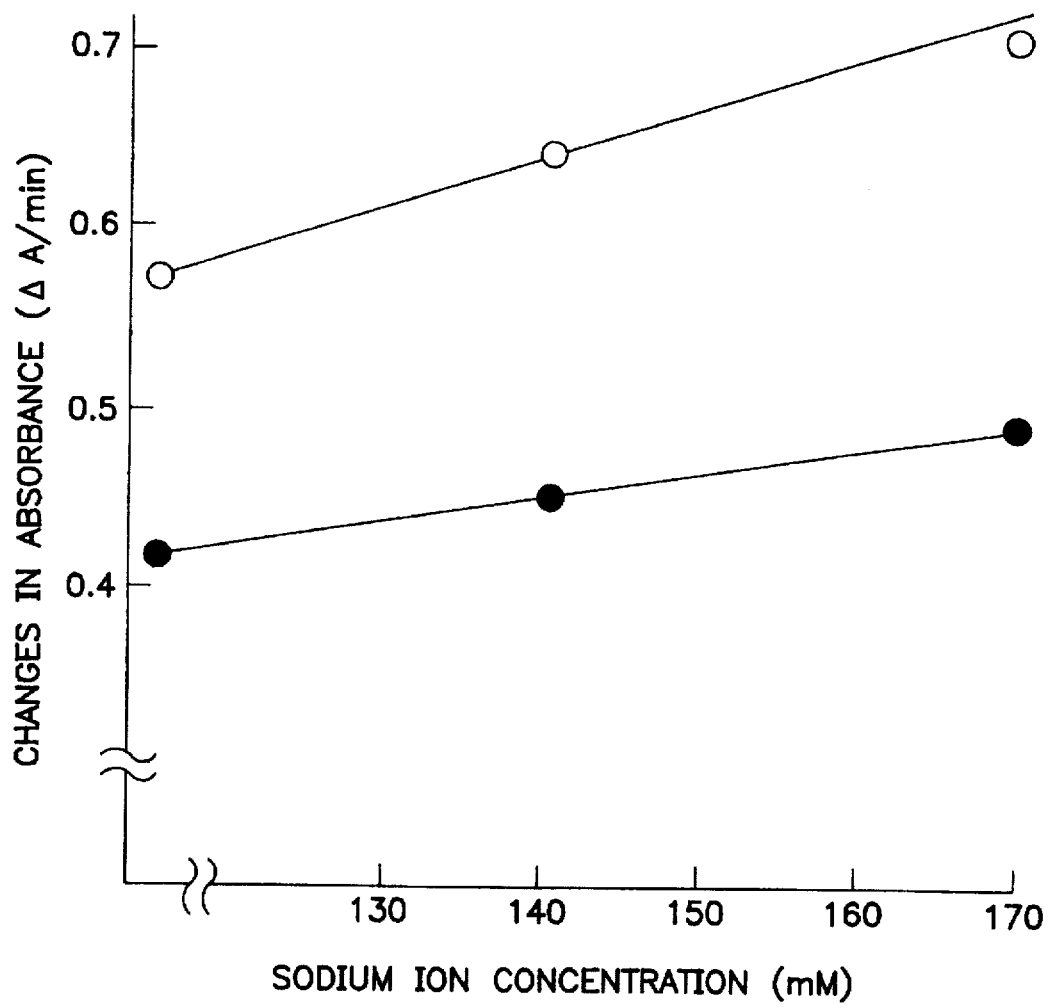
FIG. 4 shows calibration curves for sodium ions obtained by using ammonium ions. In the FIG. 4, marks -○- and -●- represent the calibration curves for sodium ions when the ammonium ion concentrations are 50 mM and 100 mM, respectively.

Sodium ions were quantitatively determined in the same manner as in Example 1 except that 50 mM or 100 mM ammonium chloride was used instead of lithium chloride. The calibration curves obtained are shown in FIG. 4.

(EXAMPLE 5)

Figure 5:
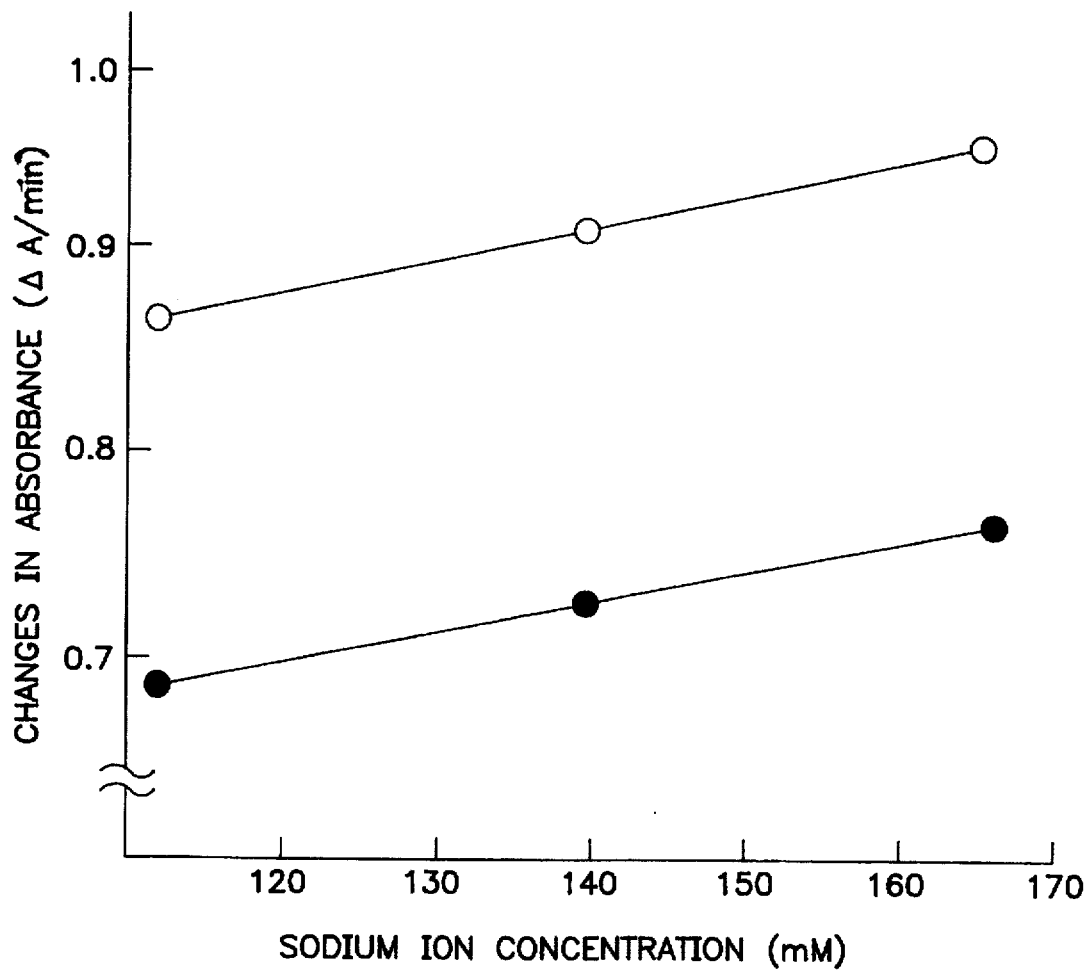
FIG. 5 shows calibration curves for sodium ions obtained by using cesium ions. In the FIG. 5, marks -○- and -●- represent the calibration curves for sodium ions when the cesium ion concentrations are 140 mM and 270 mM, respectively.

Sodium ions were quantitatively determined in the same manner as in Example 1 except that 140 mM or 270 mM cesium chloride was used instead of lithium chloride. The calibration curves obtained are shown in FIG. 5.

(EXAMPLE 6)

Sodium ions were quantitatively determined in the same manner as in Example 1 except that two serum samples obtained from humans were used as samples instead of the standard solution for the sodium ion calibration curves; that 3 mM o-nitrophenyl β-D-pyranoglycoside was used; and that HSA was added to the reaction solution at a concentration of 1.5 g/l. The results are shown in Table 1.

TABLE 1

| Serum | Measured Value (mM) | | |
|---|---|---|---|
| (Sample No.) | Example 1 | Example 2 | Flame Photometry |
| Sample 1 | 132 | 134 | 135 |
| Sample 2 | 148 | 146 | 150 |

As Table 1 clearly shows, the measured values from the method of the present invention correspond with the measured values from the flame photometry.

(EXAMPLE 7)

A sodium ion standard solution of 150 mM was measured (n=10) in the same manner as in Example 1 except that 150 mM potassium chloride was used instead of lithium chloride and that the o-nitrophenyl β-D-pyranoglycoside concentration was 2 mM. As a result, the coefficient of variation (hereinafter referred to as "CV") in the measured values was 1.5–2.8%.

(EXAMPLE 8)

The CV in sodium ion values determined was measured in the same manner as in Example 7 except that the potassium chloride concentration was 75 mM and that 19 mM 18-crown-6 was added together with potassium chloride. As a result, the CV was 0.63–0.88%.

(EXAMPLE 9)

A sodium ion standard solution of 150 mM was measured (n=10) in the same manner as in Example 1 except that the lithium chloride concentration was 150 mM; that 50 mM N-[2-(methoxy)ethyl]monoaza-15-crown-5 was added together with lithium chloride; and that the o-nitrophenyl β-D-pyranoglycoside concentration was 2 mM. As a result, the CV in the measured values was 0.43–0.75%.

Industrial Applicability

According to the present invention, there is provided a method which is good in accurate determination and reproducibility and enables the simple and quick quantitative determination of sodium ions.

We claim:

1. A method for quantitatively determining sodium ion in a sample; comprising the steps of:
    admixing β-galactosidase and an aqueous medium comprising said sample;
    reacting said sample with the β-galactosidase in the presence of at least one cation selected from the group consisting of potassium ion, cesium ion and ammonium ion; and
    correlating the result of said reaction with the quantity of sodium ions in said sample.

2. The method according to claim 1, wherein said β-galactosidase is reacted in the presence of a monocyclic crown ether.

3. A method for quantitatively determining sodium ion in a sample, comprising the steps of:
    admixing β-galactosidase and an aqueous medium comprising said sample;
    reacting said sample with the β-galactosidase in the presence of lithium ion at a concentration of from 130 mM to 0.5M; and
    correlating the result of said reaction with the quantity of sodium ions in said sample.

4. The method according to claim 3, wherein said β-galactosidase is reacted in the presence of a monocyclic crown ether.

* * * * *

UNITED STATES PATENT AND TRADEMARK OFFICE
CERTIFICATE OF CORRECTION

PATENT NO. : 5,700,652

DATED : December 23, 1997

INVENTOR(S): TOSHIO TADANO ET AL.

It is certified that error appears in the above-identified patent and that said Letters Patent is hereby corrected as shown below:

<u>COLUMN 6</u>
Line 10, "sample;" should read --sample,--.

Signed and Sealed this

Twenty-eighth Day of July, 1998

*Attest:*

BRUCE LEHMAN

*Attesting Officer*     *Commissioner of Patents and Trademarks*